United States Patent
Genova et al.

(10) Patent No.: US 12,279,844 B2
(45) Date of Patent: *Apr. 22, 2025

(54) SURGICAL INSTRUMENT APPARATUS, ACTUATOR, AND DRIVE

(71) Applicant: Titan Medical Inc., Toronto (CA)

(72) Inventors: Perry A. Genova, Chapel Hill, NC (US); Aki Hannu Einari Laakso, Raleigh, NC (US)

(73) Assignee: Covidien LP, Mansfield, MA (US)

( * ) Notice: Subject to any disclaimer, the term of this patent is extended or adjusted under 35 U.S.C. 154(b) by 756 days.

This patent is subject to a terminal disclaimer.

(21) Appl. No.: 17/406,147

(22) Filed: Aug. 19, 2021

(65) Prior Publication Data

US 2021/0378772 A1     Dec. 9, 2021

Related U.S. Application Data

(63) Continuation of application No. 16/427,164, filed on May 30, 2019, now Pat. No. 11,123,146.

(51) Int. Cl.
*A61B 17/29*     (2006.01)
*A61B 17/00*     (2006.01)
(Continued)

(52) U.S. Cl.
CPC ........ *A61B 34/71* (2016.02); *A61B 17/00234* (2013.01); *A61B 17/29* (2013.01);
(Continued)

(58) Field of Classification Search
CPC ....................... A61B 1/00149; A61B 1/005–01
See application file for complete search history.

(56) References Cited

U.S. PATENT DOCUMENTS 5,441,483 A * 8/1995 Avitall ............... A61B 18/1492
                                                    604/95.05
5,448,989 A    9/1995 Heckele
(Continued)

FOREIGN PATENT DOCUMENTS

EP    1915966 A1    4/2008
EP    3203924 A2    8/2017
(Continued)

OTHER PUBLICATIONS

International Search Report dated Aug. 25, 2020 and Written Opinion completed Aug. 10, 2020 corresponding to counterpart Int'l Patent Application PCT/CA2020/050755.
(Continued)

*Primary Examiner* — Elizabeth Houston
*Assistant Examiner* — Jonathan A Hollm
(74) *Attorney, Agent, or Firm* — Carter, DeLuca & Farrell LLP

(57) ABSTRACT

A surgical instrument apparatus for performing a surgical procedure within a body cavity of a patient is disclosed and includes an elongate manipulator having a distal end for receiving an end effector and including a plurality of control links extending through the manipulator operable to cause movement of the distal end in response to movement of the control links in a longitudinal direction. An actuator chassis is disposed at a proximal end of the manipulator and includes a plurality of actuators slidingly mounted within the actuator chassis for linear movement in the longitudinal direction. Each actuator is coupled to a control link and adjacently disposed about a curved periphery of the actuator chassis. An outwardly oriented portion couples a drive force to the actuator to cause movement of the control link.

15 Claims, 6 Drawing Sheets

(51) Int. Cl.
*A61B 34/00* (2016.01)
*A61B 34/30* (2016.01)

(52) U.S. Cl.
CPC .......... *A61B 17/2909* (2013.01); *A61B 34/30* (2016.02); *A61B 2017/00314* (2013.01); *A61B 2017/00327* (2013.01); *A61B 2017/2902* (2013.01); *A61B 2017/2908* (2013.01); *A61B 2034/306* (2016.02)

(56) References Cited

U.S. PATENT DOCUMENTS

| | | | |
|---|---|---|---|
| 5,636,780 A | 6/1997 | Green et al. | |
| 5,716,354 A | 2/1998 | Hluchy | |
| 6,331,181 B1 | 12/2001 | Tierney et al. | |
| 6,645,160 B1* | 11/2003 | Heesch | A61M 25/0133 |
| | | | 128/207.14 |
| 7,056,314 B1* | 6/2006 | Florio | A61M 25/0147 |
| | | | 604/95.01 |
| 7,147,650 B2 | 12/2006 | Lee | |
| 7,320,700 B2 | 1/2008 | Cooper et al. | |
| 7,364,582 B2 | 4/2008 | Lee | |
| 7,367,973 B2 | 5/2008 | Manzo et al. | |
| 8,142,447 B2 | 3/2012 | Cooper et al. | |
| 8,347,754 B1 | 1/2013 | Veltri et al. | |
| 8,784,435 B2 | 7/2014 | Cooper et al. | |
| 9,033,998 B1 | 5/2015 | Schaible | |
| 9,629,688 B2 | 4/2017 | Robert et al. | |
| 9,901,410 B2 | 2/2018 | Oyola | |
| 10,278,683 B2 | 5/2019 | Robert et al. | |
| 10,813,712 B2 | 10/2020 | Robert et al. | |
| 11,026,666 B2 | 6/2021 | Robert et al. | |
| 11,123,146 B2 | 9/2021 | Genova et al. | |
| 2003/0045778 A1 | 3/2003 | Ohline et al. | |
| 2003/0135204 A1 | 7/2003 | Lee et al. | |
| 2004/0193146 A1 | 9/2004 | Lee et al. | |
| 2004/0199052 A1 | 10/2004 | Banik et al. | |
| 2005/0059960 A1 | 3/2005 | Simaan et al. | |
| 2005/0096502 A1 | 5/2005 | Khalili | |
| 2005/0096694 A1 | 5/2005 | Lee | |
| 2005/0251112 A1 | 11/2005 | Danitz et al. | |
| 2005/0273085 A1 | 12/2005 | Hinman et al. | |
| 2006/0199999 A1 | 9/2006 | Ikeda et al. | |
| 2006/0235436 A1 | 10/2006 | Anderson | |
| 2007/0135803 A1 | 6/2007 | Belson | |
| 2007/0260114 A1* | 11/2007 | Miyamoto | A61B 90/36 |
| | | | 600/114 |
| 2008/0039255 A1 | 2/2008 | Jinno | |
| 2008/0045803 A1 | 2/2008 | Williams et al. | |
| 2008/0064921 A1 | 3/2008 | Larkin | |
| 2009/0171374 A1 | 7/2009 | Omori | |
| 2009/0299344 A1 | 12/2009 | Lee et al. | |
| 2010/0004509 A1 | 1/2010 | Naito et al. | |
| 2010/0234687 A1* | 9/2010 | Azarbarzin | A61B 17/00234 |
| | | | 606/1 |
| 2010/0274087 A1 | 10/2010 | Diolaiti et al. | |
| 2011/0092963 A1* | 4/2011 | Castro | A61B 17/3423 |
| | | | 606/1 |
| 2011/0290853 A1 | 12/2011 | Shelton, IV et al. | |
| 2011/0290855 A1 | 12/2011 | Moore et al. | |
| 2011/0295242 A1 | 12/2011 | Spivey et al. | |
| 2012/0071752 A1 | 3/2012 | Sewell | |
| 2012/0232339 A1 | 9/2012 | Csiky | |
| 2012/0253131 A1 | 10/2012 | Malkowski et al. | |
| 2012/0253325 A1 | 10/2012 | Sniffin et al. | |
| 2012/0298719 A1 | 11/2012 | Shelton, IV et al. | |
| 2013/0023923 A1 | 1/2013 | Mueller | |
| 2013/0041314 A1* | 2/2013 | Dillon | A61M 25/0147 |
| | | | 604/95.04 |
| 2013/0165854 A1 | 6/2013 | Sandhu et al. | |
| 2014/0001231 A1 | 1/2014 | Shelton, IV et al. | |
| 2014/0001235 A1 | 1/2014 | Shelton, IV | |
| 2014/0005653 A1 | 1/2014 | Shelton, IV et al. | |
| 2014/0005678 A1 | 1/2014 | Shelton, IV et al. | |
| 2014/0005703 A1 | 1/2014 | Stulen | |
| 2014/0046305 A1 | 2/2014 | Castro | |
| 2014/0135793 A1 | 5/2014 | Cooper et al. | |
| 2014/0276722 A1 | 9/2014 | Parihar | |
| 2014/0276931 A1 | 9/2014 | Parihar et al. | |
| 2014/0276950 A1 | 9/2014 | Smaby et al. | |
| 2016/0296219 A1 | 10/2016 | Srivastava | |

FOREIGN PATENT DOCUMENTS

| | | |
|---|---|---|
| JP | 2008220971 A | 9/2008 |
| WO | 03001987 A2 | 1/2003 |
| WO | 2006057702 A2 | 6/2006 |
| WO | 2010098871 A2 | 9/2010 |
| WO | 2012078309 A2 | 6/2012 |
| WO | 2012138834 A2 | 10/2012 |
| WO | 2013082310 A1 | 6/2013 |
| WO | 2014201538 A1 | 12/2014 |
| WO | 2016183054 A1 | 11/2016 |
| WO | 2017098271 A1 | 6/2017 |
| WO | 2018053305 A1 | 3/2018 |
| WO | 2018065490 A2 | 4/2018 |
| WO | 2018207136 A1 | 11/2018 |
| WO | 2018211730 A1 | 11/2018 |

OTHER PUBLICATIONS

Decision to Grant European patent received in European Application No. 13887243.7, dated May 11, 2017.
Extended European Search Report and Written Opinion received in European Application No. 17171068.4, dated Sep. 28, 2017.
Notice of Allowance received in Canadian Application No. 2,913,943, dated Apr. 24, 2018.
Examiner Requisition received in Canadian Application No. 2,913,943, dated Jan. 16, 2017.
Examiner Requisition received in Canadian Application No. 2,913,943, dated Jun. 6, 2017.
Examiner Requisition received in Canadian Application No. 2,913,943, dated Dec. 29, 2017.
Written Opinion received in PCT Application No. PCT/CA2013/001076, dated Feb. 19, 2014 in 6 pages.
International Search Report mailed by Canadian Intellectual Property Office dated Mar. 5, 2014 in PCT Application No. PCT/CA2013/001076 in 5 pages.
International Search Report for International Application No. PCT/CA2015/000098 dated Jul. 29, 2015, in 13 pages.
Written Opinion for International Application No. PCT/CA2015/000098 dated Jul. 29, 2015, in 5 pages.
Examination Report in European Application No. 15866790.7 dated Apr. 18, 2018 in 7 pages.
Extended European Search Report issued by European Patent Office dated May 23, 2016 in the corresponding European Patent Application 13887243.7 in 9 pages.
Chinese Office Action dated Jan. 19, 2024 issued in corresponding Chinese Patent Application No. 2020800242288 (12 pages).
Extended European Search Report dated Aug. 21, 2023 for European Patent Application No. 20814661.3 (12 pages).
Office Action dated Feb. 26, 2024 issued in Canadian Patent Application No. 3,133,781 (4 pages).

* cited by examiner

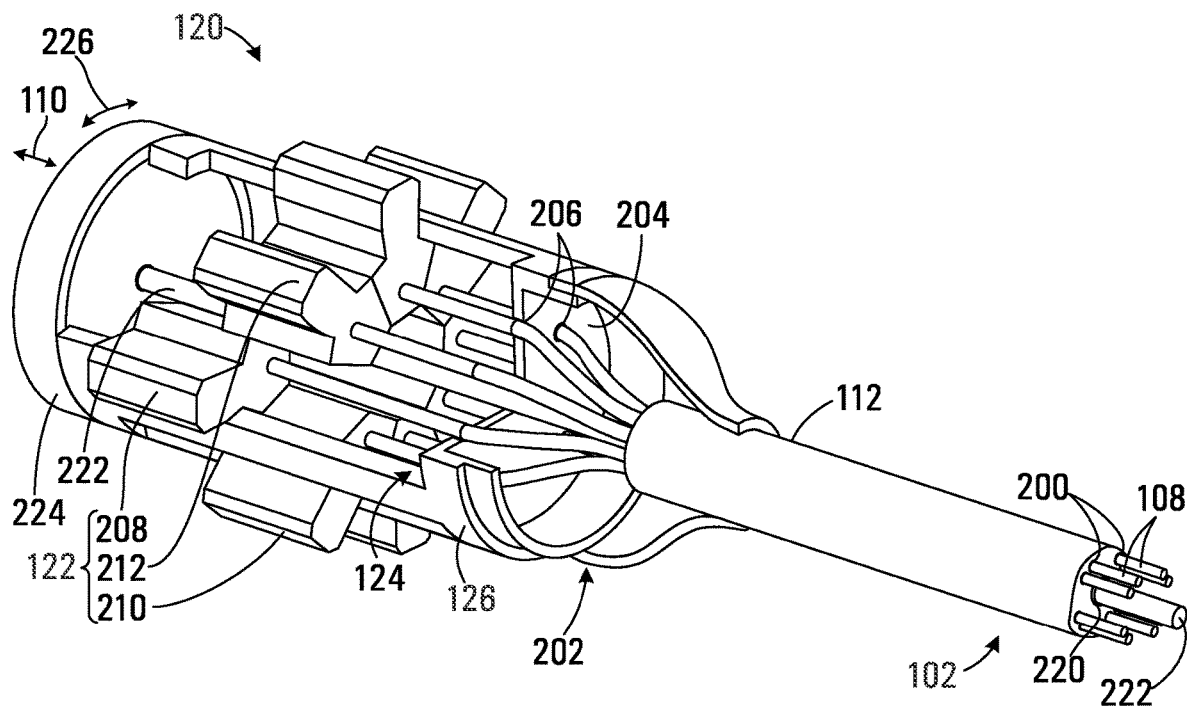
FIG. 2
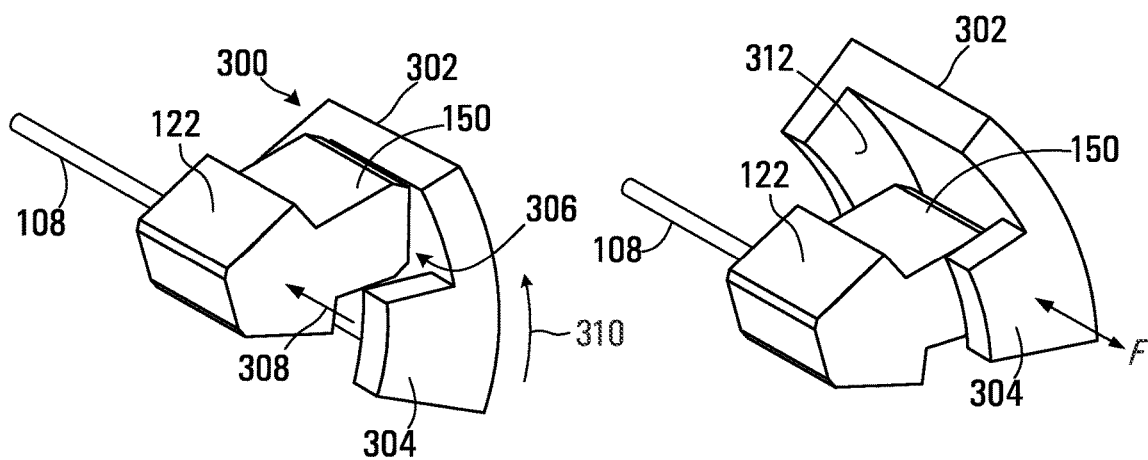
FIG. 3A  FIG. 3B

SURGICAL INSTRUMENT APPARATUS, ACTUATOR, AND DRIVE

CROSS-REFERENCE TO RELATED APPLICATION

The present application is a Continuation Application claiming the benefit of and priority to U.S. patent application Ser. No. 16/427,164, filed on May 30, 2019, the entire content of which is incorporated herein by reference.

TECHNICAL FIELD

This disclosure relates generally to a surgical instrument apparatus for performing a surgical procedure within a body cavity of a patient.

DESCRIPTION OF RELATED ART

Surgical instruments used in laparoscopic and/or robotic surgery generally have a proximally located actuator that may be used to actuate a distal end effector for performing a surgical task within a body cavity of a patient. Such instruments may be used in applications where there is an area of limited access for an operator. The distal end of the instrument may be inserted into the area of limited access and the operator may remotely manipulate the instrument via the actuator. The actuator may be located outside the area of limited access, but there may still be constraints placed on the extents of the actuator. There remains a need for actuators and drivers that are suitable for laparoscopic and/or robotic instruments.

SUMMARY

In accordance with one disclosed aspect there is provided a surgical instrument apparatus for performing a surgical procedure within a body cavity of a patient. The apparatus can include an elongate manipulator with a distal end configured to receive an end effector and including a plurality of control links extending through the manipulator and configured to cause movement of the distal end of the manipulator in response to movement of the control links in a longitudinal direction generally aligned with a length of the manipulator. The apparatus can also include an actuator chassis disposed at a proximal end of the manipulator, the actuator chassis including a plurality of actuators slidingly mounted within the actuator chassis and configured to move linearly in a direction aligned with the longitudinal direction, each actuator being coupled to one of the control links. The actuators are adjacently disposed about a curved periphery of the actuator chassis and including an outwardly oriented portion configured to couple a drive force to the actuator to cause movement of the control link.

The curved periphery of the actuator chassis may be cylindrically shaped and the plurality of actuators may be mounted within slots extending longitudinally along the periphery and radially arranged about the periphery.

The actuator chassis periphery may include a curved portion and a flat portion and the plurality of actuators may be mounted within slots extending longitudinally along the curved portion and radially arranged about the curved portion, the flat portion facilitating location of the surgical instrument apparatus adjacent (for example, closely adjacent) to another apparatus including a corresponding flat portion.

The another apparatus including the corresponding flat portion may include another of the surgical instrument apparatus and the respective flat portions may facilitate location of the respective elongate manipulators in proximity (for example, close proximity) for insertion through a common access port inserted or positioned to provide access to the body cavity of the patient.

The outwardly oriented portions of the plurality of actuators may be each shaped to engage a corresponding drive coupler configured to couple the drive force to the actuator.

The actuator coupling portion of the actuator may include a protrusion that extends outwardly beyond the curved periphery of the actuator chassis.

The apparatus may include a drive chassis including a respective plurality of drive couplers configured to couple drive forces to the plurality of actuators, the drive couplers arranged about the periphery of the actuator chassis, each drive coupler may include an open channel portion configured to receive the respective actuator protrusions when the actuator chassis is inserted into the drive chassis, and a retaining portion configured to receive and retain the respective actuator protrusions when the drive chassis and the actuator chassis are rotated thorough an angle to cause the retaining portions to engage the respective actuator protrusions.

The drive chassis may be configured to permit the manipulator to be inserted through the drive chassis to cause the open channel portions to receive the respective actuator protrusions.

The actuator chassis may include a transition portion between the manipulator and the actuator chassis, the transition portion configured to laterally displace the control links for coupling to the respective actuators.

The manipulator may include at least one end effector control link configured to couple to an end effector and the actuator chassis may include at least one end effector actuator coupled to the end effector control link to actuate movements of the end effector.

The at least one end effector actuator may be mounted within the actuator chassis to permit at least one of longitudinal movement configured to actuate opening or closing of an end effector, or rotational movement configured to cause a corresponding rotation of the end effector.

The at least one end effector actuator may include a single end effector actuator configured to perform both the longitudinal movement and the rotational movement.

The at least one end effector control link may be routed along a central bore of the actuator chassis and the end effector actuator may be mounted at a distal portion of the actuator chassis.

The manipulator may include a rigid portion connected to the actuator chassis, and an actuatable articulated portion configured to cause the movement of the distal end of the manipulator in response to the longitudinal movement of the control links.

The apparatus may include an unactuated articulated portion disposed between the rigid portion and the chassis, the unactuated articulated portion configured to permit the manipulator to be bent to reduce an overall length of the manipulator and actuator chassis during cleaning and sanitizing of the apparatus.

In accordance with another disclosed aspect there is provided a surgical instrument apparatus for performing a surgical procedure within a body cavity of a patient. The apparatus can include an elongate manipulator with a distal end configured to receive an end effector and including a plurality of control links extending through the manipulator and configured to cause movement of a distal end of the manipulator in response to movement of the control links in a longitudinal direction generally aligned with a length of the manipulator. The apparatus can also include an actuator chassis disposed at a proximal end of the manipulator, the actuator chassis including a plurality of actuators mounted within the actuator chassis, each actuator being coupled to one of the control links configured to couple a drive force to the actuator to cause movement of the control link. The proximate end of the manipulator can be laterally offset to facilitate location or positioning of the surgical instrument apparatus adjacent (such as, closely adjacent) to another surgical instrument apparatus for insertion or positioning through a common access port inserted to provide access to the body cavity of the patient.

The manipulator may include a rigid portion connected to the actuator chassis, and an actuatable articulated portion configured to cause the movement of the distal end of the manipulator in response to longitudinal movement of the control links.

The apparatus may include an unactuated articulated portion disposed between the rigid portion and the actuator chassis, the unactuated articulated portion configured to permit the manipulator to be bent to reduce an overall length of the manipulator and actuator chassis during cleaning and sanitizing of the apparatus.

The proximate end of the manipulator can be laterally offset to facilitate positioning of the surgical instrument adjacent to the another surgical instrument apparatus so that spacing between the manipulator and another manipulator of the another surgical instrument is between about 10 millimeters and about 35 millimeters.

In accordance with another disclosed aspect there is provided a surgical instrument apparatus for performing a surgical procedure within a body cavity of a patient. The apparatus can include an elongate manipulator with a distal end configured to receive an end effector and including a plurality of control links extending through the manipulator and configured to cause movement of a distal end of the manipulator in response to movement of the control links in a longitudinal direction generally aligned with a length of the manipulator. The apparatus can also include an actuator chassis disposed at a proximal end of the manipulator, the actuator chassis including a plurality of actuators mounted within the actuator chassis, each of the plurality of actuators being coupled to one of the control links configured to couple a drive force to the actuator to cause movement of the control link. The manipulator can include a rigid portion connected to the actuator chassis, and an actuatable articulated portion configured to cause the movement of the distal end of the manipulator in response to longitudinal movement of the control links. The apparatus can further include an unactuated articulated portion disposed between the rigid portion and the chassis, the unactuated articulated portion configured to permit the manipulator to be bent to reduce an overall length of the manipulator and actuator chassis during cleaning and sanitizing of the apparatus.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments,

FIG. 2 is a partially cut away perspective view of an actuator chassis of the surgical instrument apparatus shown in FIG. 1;

FIG. 3A is a perspective view of an actuator of the actuator chassis shown in partial engagement with a drive coupler;

FIG. 3B is a perspective view of the actuator shown in full engagement with the drive coupler;

DETAILED DESCRIPTION

Figure 1:
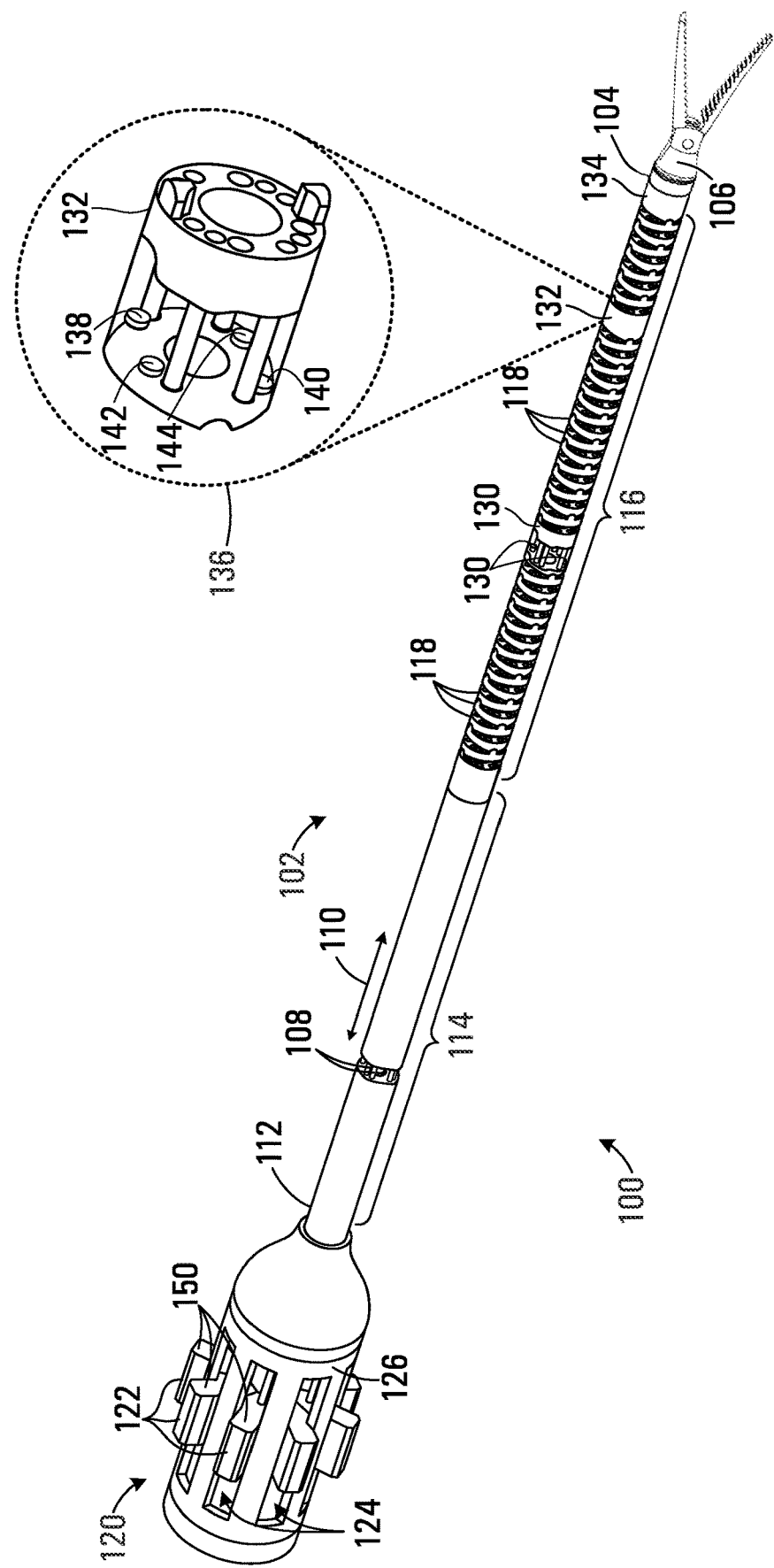
FIG. 1 is a perspective view of a surgical instrument apparatus for performing a surgical procedure within a body cavity of a patient.

Referring to FIG. 1, a surgical instrument apparatus for performing a surgical procedure within a body cavity of a patient is shown generally at 100. The apparatus 100 includes an elongate manipulator 102 having a distal end 104 for receiving an end effector 106. The manipulator 102 includes a plurality of control links 108 extending through the manipulator. The plurality of control links 108 are operable to cause movement of the distal end 104 of the manipulator in response to movement of the control links in a longitudinal direction 110 generally aligned with a length of the manipulator. The apparatus 100 also includes an actuator chassis 120 disposed at a proximal end 112 of the manipulator 102. The actuator chassis 120 includes a plurality of actuators 122 slidingly mounted within the actuator chassis for linear movement in a direction aligned with the longitudinal direction 110. In the embodiment shown, the actuators 122 are adjacently mounted within respective slots 124 disposed on a curved periphery 126 of the actuator chassis 120.

In the embodiment shown, the manipulator 102 includes a rigid portion 114 connected to the actuator chassis 120 and an articulated portion 116 that is actuatable to cause the movement of the distal end 104 of the manipulator in response to the longitudinal movement of the control links 108. The articulated portion 116 includes a plurality of coupled guides 118 mounted end-to-end and operable to move in response to pulling or pushing of the plurality of control links 108 as described in commonly owned PCT patent publication WO2014/201538 entitled "ARTICULATED TOOL POSITIONER AND SYSTEM EMPLOYING SAME" filed on Dec. 20, 2013 and incorporated herein by reference in its entirety. In other embodiments, the manipulator 102 may include structures other than the coupled guides 118 for causing movement of the distal end 104 of the manipulator.

Referring to FIG. 2, the proximal end 112 of the manipulator 102 and the actuator chassis 120 are shown with the actuator chassis partially cut away. In one embodiment, the plurality of control links 108 are implemented as wires routed through respective bores 200 extending through the manipulator 102. The actuator chassis 120 has a transition portion 202 between the proximal end 112 of the manipulator 102 and the actuator chassis. In this embodiment the transition portion 202 includes a bulkhead 204 having openings 206 that cause the respective control links 108 to be laterally displaced toward the curved periphery 126 of the actuator chassis 120. The transition portion 202 facilitates the movement of the control links 108 along their respective axes while preventing drift of the control links 108. In one embodiment, the transition portion 202 may include curved conduit (not shown) extending between the proximal end 112 of the manipulator 102 and the bulkhead 204 for receiving and guiding control links 108 through the transition portion. Each actuator 122 is coupled to one of the control links 108. The control links 108 may be implemented using nitinol wire, which is capable of bending through an arc while still transmitting force in tension or compression. Nitinol is an alloy of nickel and titanium having shape memory and superelasticity and is capable of transmitting forces of about 200 N. In other embodiments, the control links 108 may be implemented using other commonly used wires such as stranded cables used in laparoscopic instruments.

One actuator 208 of the plurality of actuators 122 is shown displaced longitudinally within the slot 124. The longitudinal displacement of the actuator 208 causes the coupled control link 108 to be correspondingly pulled rearwardly within the actuator chassis 120. Other actuators 122 such as the adjacent actuators 210 and 212 are similarly moveable within the respective slots 124 to push or pull the associated control link 108. In the embodiment shown, the curved periphery 126 of the actuator chassis 120 is cylindrically shaped and the slots 124 are radially arranged about the curved periphery.

Referring back to FIG. 1, in one embodiment pairs of the control links 108 are coupled to coupler segments 130, 132, and 134. Actuation of the control links 108 by the actuators 122 causes the coupled guides 118 between each of the coupler segments to be displaced laterally to cause the distal end 104 and the end effector 106 to be moved into a desired position and orientation. A portion of the coupler segment 132 is shown cut away in an insert 136. In this embodiment a first pair 138, 140 of the plurality of control links 108 terminate within the coupler segment 132 and when the control link 138 is pushed by advancing the associated actuator 122 while the control link 140 is pulled by rearwardly retracting the associated actuator 122 within its slot, the coupler segment 132 is moved laterally. Similarly, a second pair 142, 144 of the plurality of control links 108 terminate within the coupler segment 132 and when the control link 142 is pushed by advancing the associated actuator 122 within its slot while the control link 144 is pulled by rearwardly retracting the associated actuator 122 within its slot, the coupler segment 132 is moved vertically upward. Reversal of the pushing and pulling of the respective actuators 122 causes a respective lateral movement to the opposite side or downward movement.

In another embodiment, the first pair 138, 140 of the plurality of control links 108 may be respectively used for pulling motions without a corresponding pushing motion. In this embodiment when the control link 140 is pulled by rearwardly retracting the associated actuator 122 within its slot (while the control link 138 is let out by a corresponding amount, such as, for example, by advancing the associated actuator 122 or by allowing the actuator 122 to feely float), the coupler segment 132 is moved laterally. Similarly, in another embodiment, for the second pair 142, 144 of the plurality of control links 108 when the control link 144 is pulled by rearwardly retracting the associated actuator 122 within its slot (while the control link 142 is let out by a corresponding amount, such as, for example, by advancing the associated actuator 122 or by allowing the actuator 122 to freely float), the coupler segment 132 is moved vertically upward. Reversal of the pulling of the respective actuators 122 causes a respective lateral movement to the opposite side or downward movement.

Combinations of lateral and vertical movement will cause the 132 to move in any direction within a working volume of the manipulator 102. The coupler segment 134 may be similarly moved via other pairs of control links 108 actuated by the respective actuators 122 to point in any direction within the working volume. Further as described in commonly owned PCT patent publication WO2014/201538, the coupled guides 118 between the rigid portion 114 and the coupler segment 130 and the coupled guides between the coupler segment 130 and the coupler segment 132 may be configured to maintain the orientation of the coupler segment 132 substantially the same as the rigid portion 114. In this case, the guides 118 within these portions of the articulated portion 116 are constrained to move as a two-dimensional parallelogram by a set of wire links extending between the rigid portion 114 and the coupler segment 132.

Still referring to FIG. 1, each of the actuators 122 includes an outwardly oriented portion 150 that facilitates coupling a drive force to the actuator to cause movement of the coupled control link. In this embodiment, the outwardly oriented portions 150 also protrude outwardly with respect to the curved periphery 126. Referring to FIG. 3A, one of the actuators 122 is shown in isolation in engagement with a drive coupler 300. The drive coupler 300 may be part of an instrument drive of a robotic surgery system (not shown). The drive coupler 300 includes a curved outer wall 302 and a first end wall 304 extending radially inwardly from the curved outer wall and defining an open channel 306 in the drive coupler. The open channel 306 is sized to receive the protruding portion 150 of the actuator 122 when slid into the drive coupler 300 in the direction indicated by the arrow 308 in FIG. 3A. Once received within the opening 306, the drive coupler 300 is rotated in the direction of the arrow 310 to engage the outwardly oriented portion 150 of the actuator 122 as shown in FIG. 3B.

Referring to FIG. 3B, the drive coupler 300 further includes a second end wall 312 extending over the full length of the curved outer wall 302. The outwardly oriented portion 150 of the actuator 122 is engaged between the first end wall 304 and the second end wall, which define a retaining portion for receiving and retaining the actuator protrusion 150 when the drive coupler 300 is rotated though an angle to cause the retaining portions to engage the actuator protrusion. Once the drive coupler 300 is engaged, a force F applied to the drive coupler 300 is transmitted to the outwardly oriented portion 150 to cause longitudinal motion of the actuator 122 within the associated slot 124.

Figure 4A:
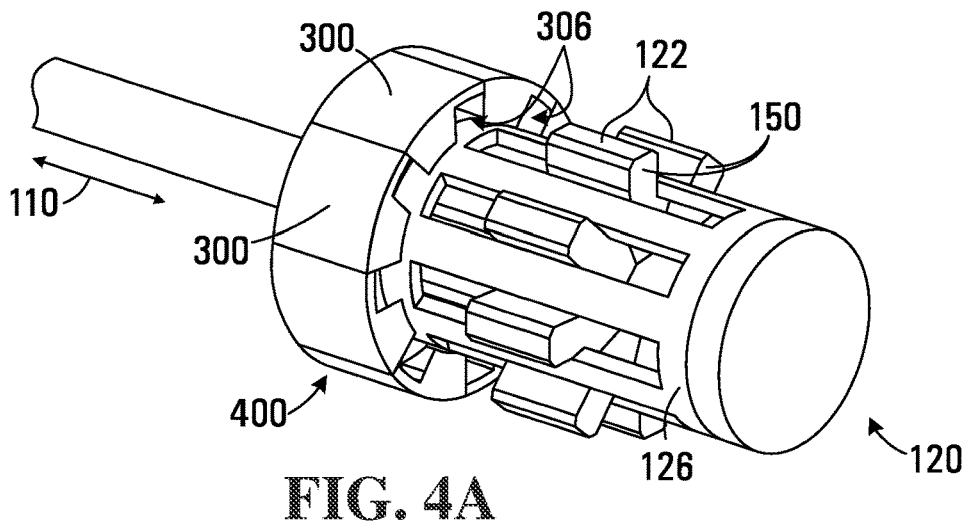
FIG. 4A is a perspective view of a drive chassis including a plurality of the drive couplers shown in FIGS. 3A and 3B and the actuator chassis of FIG. 2 being inserted into the drive chassis.
Figure 4B:
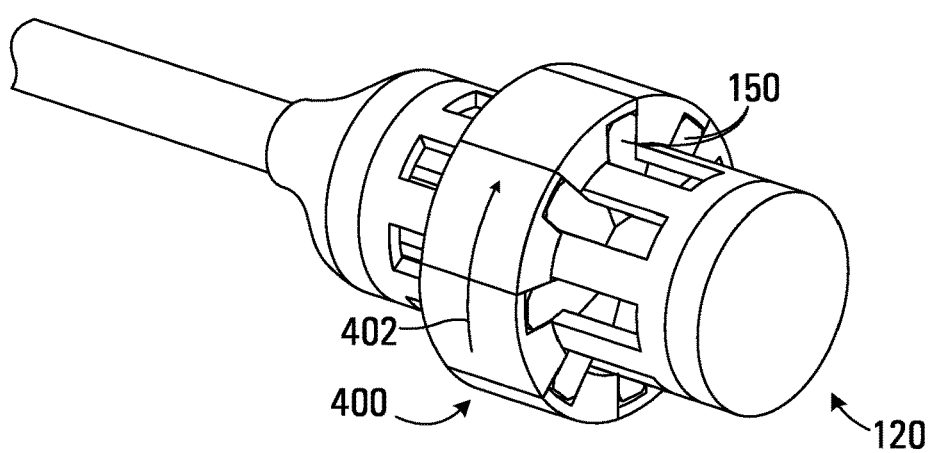
FIG. 4B is a perspective view of the drive chassis of FIG. 4A showing the actuator chassis in partial engagement with the drive chassis.
Figure 4C:
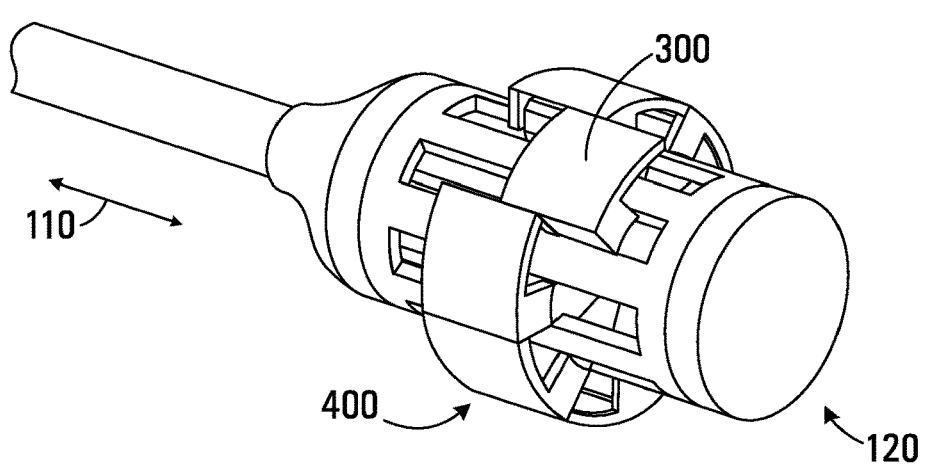
FIG. 4C is a perspective view of the drive chassis of FIG. 4B showing the actuator chassis in full engagement with the drive chassis.

Referring to FIG. 4A, in the embodiment shown a plurality of the drive couplers 300 shown in FIG. 3A and 3B are arranged to provide a drive chassis 400. The drive couplers 300 are annularly arranged about the periphery 126 of the actuator chassis 120 with the open channels 306 aligned with the outwardly oriented portions 150 of the actuators 122. The drive chassis 400 is configured to permit the manipulator 102 to be inserted through the drive chassis when loading the surgical instrument apparatus 100. The open channels 306 of the drive couplers 300 receive the respective actuator protrusions 150 as shown in FIG. 4B. Referring to FIG. 4B, the drive chassis 400 and/or actuator chassis 120 is then rotated thorough an angle in a direction indicated by the arrow 402 to cause the retaining portions (i.e. first and second end walls 304 and 312, shown in FIGS. 3A and 3B) to engage the respective actuator protrusions 150 as shown in FIG. 4C. Referring to FIG. 4C, once the drive couplers 300 are engaged, each drive coupler is able to independently move back and forward in the longitudinal direction 110 to couple drive forces to the respective actuators 122. In one embodiment the drive chassis 400 is part of an instrument drive (not shown) that generates and couples individual drive forces to the respective drive couplers 300. The instrument drive may be implemented as part of a robotic surgery system in which operator input received at an input device is used to generate drive signals, which are used to control the instrument drive for causing manipulation of the manipulator 102 via the drive chassis 400 and actuator chassis 120.

In the embodiment shown in FIG. 1, eight actuators 122 and associated control links 108 are provided. Four of these actuators 122 cause movement of the coupler segment 132, while the remaining four actuators cause movement of the coupler segment 134. Referring back to FIG. 2, the manipulator 102 further includes a central bore 220 that in this embodiment accommodates an end effector control link 222. The end effector control link 222 is coupled to the end effector 106 for causing opening of the actuator jaws and/or causing rotation of the actuator about a longitudinal axis of the manipulator 102. The end effector control link 222 is routed through the actuator chassis 120 and coupled to an end cap 224 at a distal proximal end of the actuator chassis. In one embodiment, the end cap 224 is able to rotate in the direction of the arrow 226, which rotates the end effector control link 222 causing corresponding rotation of the end effector at the distal end 104 of the manipulator 102. Additionally, the end cap 224 may also be configured to move in the longitudinal direction 110 to actuate longitudinal back and forth movement of the end effector control link 222 for opening and closing the end effector. The single end effector control link 222 may thus be operable to actuate both rotation and opening/closing movements of the end effector 106. In other embodiments, the end effector control link 222 may be configured as a hollow torque tube that provides the rotational actuation to the end effector 106, while an additional control link may be routed through the central bore 220 to actuate the opening and closing movements of the end effector 106.

Figure 5A:
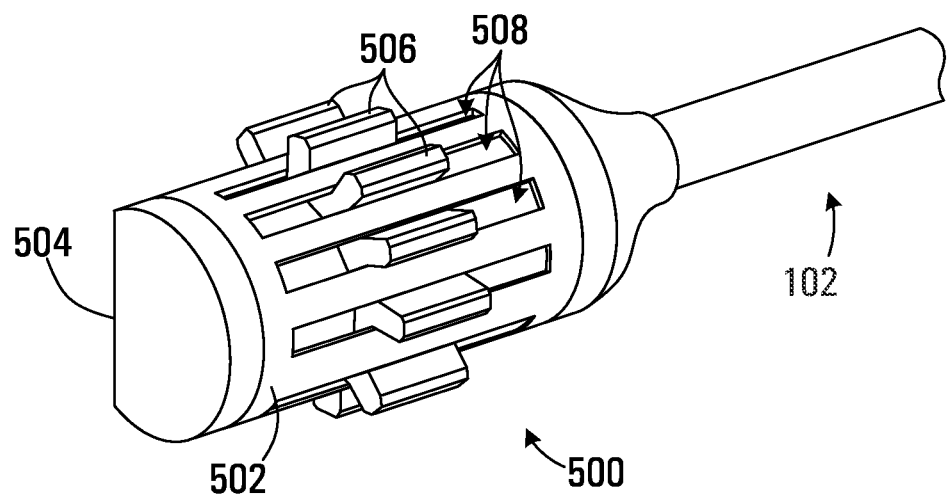
FIG. 5A is a perspective view of a surgical instrument apparatus in accordance with another embodiment.

Referring to FIG. 5A, an actuator chassis in accordance with another embodiment is shown generally at 500. The periphery of the actuator chassis 500 includes a curved portion 502 and a flat portion 504. The actuator chassis 500 includes a plurality of actuators 506 configured generally as described above. The plurality of actuators 506 are mounted in respective slots 508 extending longitudinally along the curved portion 502 of the actuator chassis 500. The actuators 506 are radially arranged about the curved portion 502 and the actuator chassis 500 is coupled to a manipulator 102 (shown in part) as generally described above.

Figure 5B:
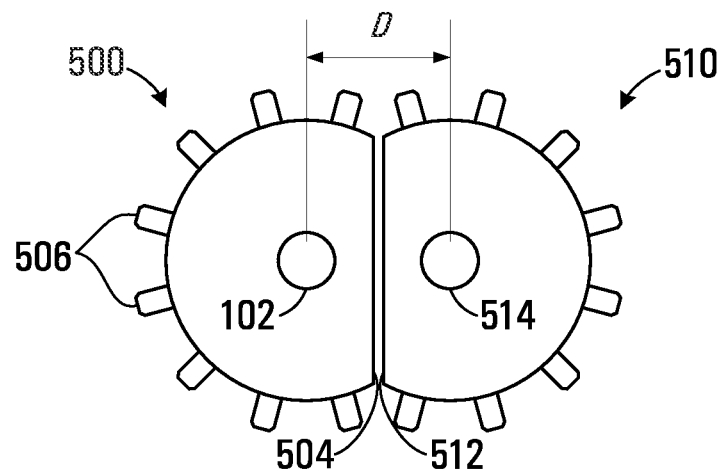
FIG. 5B is a perspective view of a pair of the surgical instrument apparatus shown in FIG. 5A disposed adjacently for insertion through a common access port.

In many cases two or more of the surgical instrument apparatus 100 may be used during a surgical procedure performed through a single common access port (i.e. a single incision or opening to a body cavity of a patient). Referring to FIG. 5B, the flat portion 504 of the actuator chassis 500 facilitates closely spacing the actuator adjacent to a second actuator chassis 510 having a corresponding flat portion 512. The close spacing has the advantage of spacing the manipulator 102 and a manipulator 514 coupled to the actuator chassis 510 in relatively close proximity for insertion through a common access port and/or trocar (not shown). The spacing D between the manipulators may be less than about 10 millimeters, about 10 millimeters, about 20 millimeters, about 21.5 millimeters, about 35 millimeters, about 40 millimeters, or greater than about 35 millimeters or 40 millimeters, such as about 50 millimeters or 60 millimeters. The spacing D between the manipulators may be between about 10 millimeters (or less) and about 20 millimeters (or more), between about 10 millimeters (or less) and about 35 millimeters (or more), between about 10 millimeters (or less) and about 40 millimeters (or more), between about 20 millimeters (or less) and about 35 millimeters (or more), or between about 20 millimeters (or less) and about 40 millimeters (or more). The further off-center the manipulator 102 and the manipulator 514 are from the respective actuator chassis 500 and 510 such that the spacing D is reduced, the smaller the diameter of the common access port/trocar. Each of the actuator chassis 500 and the actuator chassis 510 would be received within a drive chassis (not shown) configured to accommodate and provide drive forces for operating the side-by-side surgical instruments.

Figure 6:
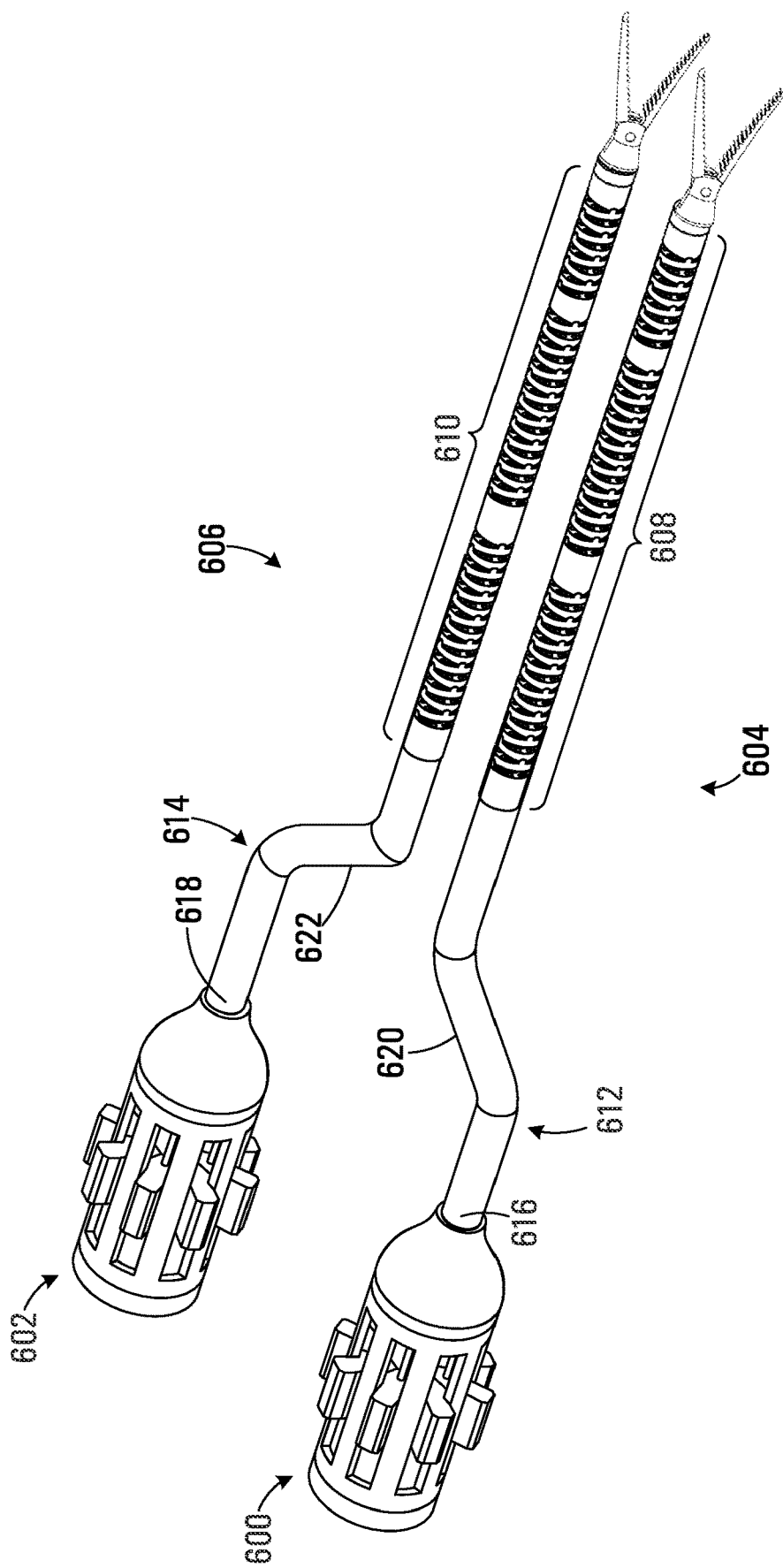
FIG. 6 is a perspective view of a pair of surgical instruments disposed adjacently for insertion through a common access port operation in accordance with another embodiment.

Referring to FIG. 6, an alternative arrangement for side-by-side surgical instrument operation includes a first actuator chassis 600 disposed spaced apart from a second actuator chassis 602. Each actuator chassis 600, 602 has a respective manipulator 604 and 606 coupled to the chassis. The manipulators 604 and 606 have respective actuatable articulated portions 608 and 610 configured generally as described above in connection with the FIG. 1 embodiment. The manipulators 604 and 606 each have respective rigid portions 612 and 614. The rigid portion 612 of the manipulator 604 has a leftward laterally offset portion 620 while the manipulator 606 has a rightward laterally offset portion 622. The left and right laterally offset portions 620 and 622 facilitate closely adjacent location of the respective articulated portions 608 and 610 of the manipulators 604 and 606 for insertion through a common access port.

Figure 7:
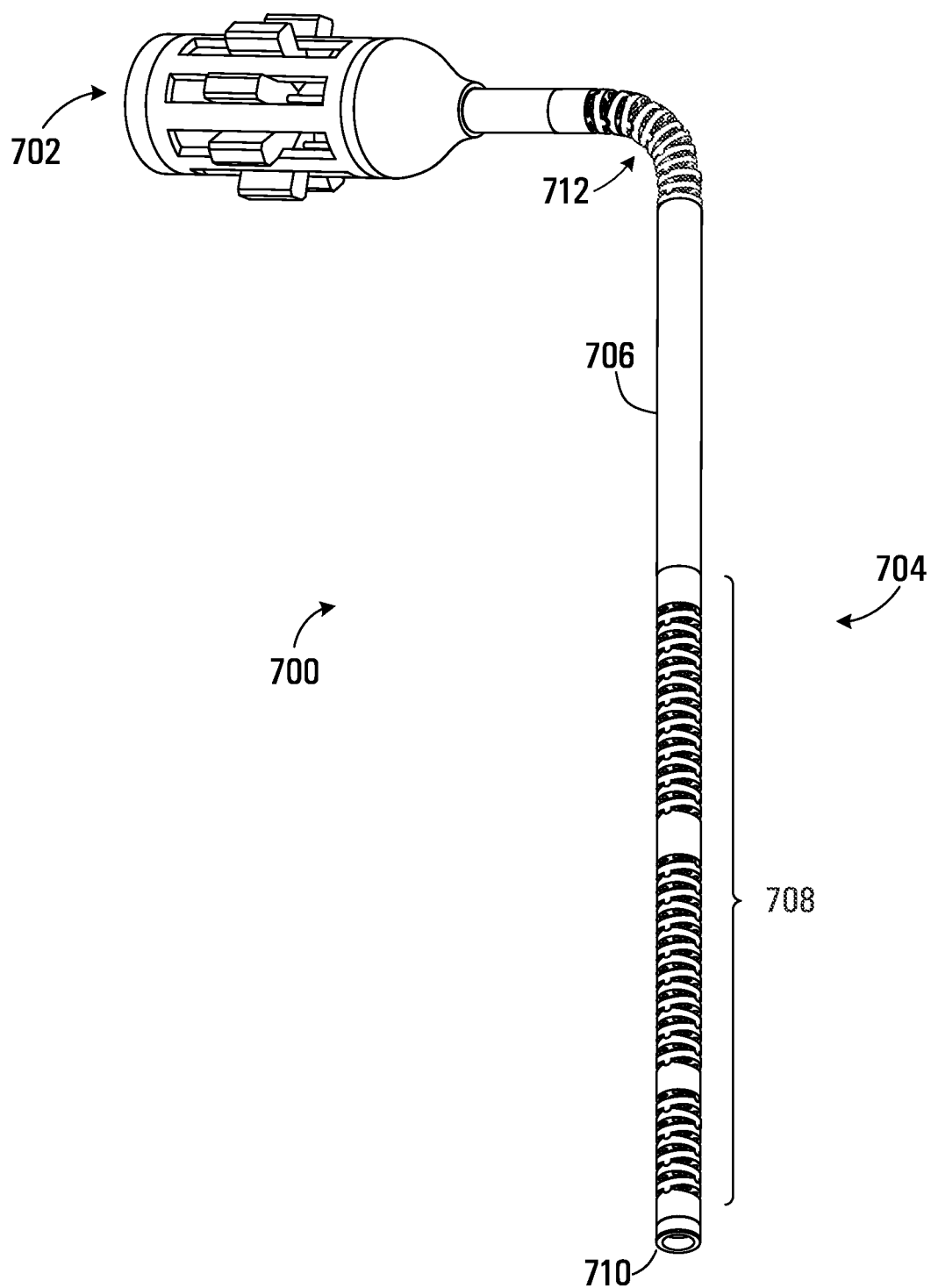
FIG. 7 is a perspective view a surgical instrument apparatus in accordance with another embodiment.

Referring to FIG. 7, a surgical instrument apparatus in accordance with another embodiment is shown generally at 700. The surgical instrument apparatus 700 includes an actuator chassis 702 configured generally as disclosed above. The actuator chassis 702 is coupled to a manipulator 704 including a rigid portion 706 and an actuatable articulated portion 708 also configured generally as disclosed above. In this embodiment, the surgical instrument apparatus 700 further includes an articulated portion 712 disposed between the rigid portion 706 and the actuator chassis 702. The articulated portion 712 permits the manipulator to be bent as shown in FIG. 7 to reduce an overall length of the instrument (i.e. manipulator and actuator chassis). The articulated portion 712 may be actuated during a surgical procedure or may be a passive portion that is not actuated during the procedure.

In many cases the surgical instrument apparatus 700 may be reusable and cleaning and sanitization following use in a surgical procedure is thus required. The overall length of the surgical instrument apparatus 100 shown in FIG. 1 may prohibit its accommodation within the conventional sanitization equipment. The articulated portion 712 facilitates bending of the instrument to reduce the overall dimensions that may make the instrument more readily accommodated in a decontamination sink or a chamber of a washer/disinfector commonly used for cleaning and sanitization in surgical environments. Additional bending to accommodate limited space constraints during cleaning and sanitization may be enabled by having the actuatable articulated portion 708 at least partially bendable/flexible during cleaning and sanitization (i.e. when not in surgical use). This additional bending and/or the bending of articulated portion 712 may be facilitated by may allowing the control links extending through the manipulator 704 to move into a relaxed state, for example by maneuvering the actuators (such as actuators 506 shown in FIG. 5A).

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, or within less than 0.01% of the stated value.

While specific embodiments have been described and illustrated, such embodiments should be considered illustrative only and not as limiting the disclosed embodiments as construed in accordance with the accompanying claims.

What is claimed is:

1. A surgical instrument apparatus for performing a surgical procedure within a body cavity of a patient, the apparatus comprising:
    an elongate manipulator including a distal end configured to receive an end effector and including a plurality of control links extending through the manipulator and configured to cause movement of the distal end of the manipulator in response to movement of the control links in a longitudinal direction generally aligned with a length of the manipulator, wherein the elongate manipulator defines a manipulator central longitudinal axis; and
    an actuator chassis disposed at a proximal end of the manipulator, the actuator chassis including a plurality of actuators mounted within the actuator chassis, each actuator being coupled to one of the control links configured to couple a drive force to the actuator to cause movement of the control link, wherein the actuator chassis defines a chassis central longitudinal axis, wherein a periphery of the actuator chassis includes a curved portion and a flat portion, and wherein the plurality of actuators are mounted within slots extending longitudinally along the curved portion and radially arranged about the curved portion, the flat portion facilitating location of the surgical instrument apparatus adjacent to another apparatus including a corresponding flat portion,
    wherein the manipulator central longitudinal axis is parallel with and laterally offset from the chassis central longitudinal axis to facilitate positioning of the surgical instrument apparatus adjacent to another surgical instrument apparatus for insertion through a common access port positioned to provide access to the body cavity of the patient.

2. The apparatus of claim 1 wherein the manipulator comprises:
    a rigid portion connected to the actuator chassis; and
    an actuatable articulated portion configured to cause the movement of the distal end of the manipulator in response to longitudinal movement of the control links.

3. The apparatus of claim 2 further comprising an unactuated articulated portion disposed between the rigid portion and the actuator chassis, the unactuated articulated portion configured to permit the manipulator to be bent to reduce an overall length of the manipulator and actuator chassis during cleaning and sanitizing of the apparatus.

4. The apparatus of claim 1 wherein the proximate end of the manipulator is laterally offset to facilitate positioning of the surgical instrument apparatus adjacent to the another surgical instrument apparatus so that spacing between the manipulator and another manipulator of the another surgical instrument is between 10 millimeters and 35 millimeters.

5. A surgical instrument apparatus for performing a surgical procedure within a body cavity of a patient, the apparatus comprising:
    an elongate manipulator comprising a distal end configured to receive an end effector and including a plurality of control links extending through the manipulator and configured to cause movement of the distal end of the manipulator in response to movement of the control links in a longitudinal direction generally aligned with a length of the manipulator, wherein the elongate manipulator defines a manipulator central longitudinal axis; and
    an actuator chassis disposed at a proximal end of the manipulator, wherein a periphery of the actuator chassis includes a curved portion and a flat portion, the actuator chassis including a plurality of actuators slidingly mounted with respect to the actuator chassis and configured to move linearly in a direction aligned with the longitudinal direction, each actuator being coupled to one of the control links, the actuators being disposed about the periphery of the actuator chassis and including an outwardly oriented portion configured to couple a drive force to the actuator to cause movement of the control link, wherein the actuator chassis defines a chassis central longitudinal axis, wherein the plurality of actuators are mounted within slots extending longitudinally along the curved portion and radially arranged about the curved portion, the flat portion facilitating location of the surgical instrument apparatus adjacent to another apparatus including a corresponding flat portion, and wherein the manipulator central longitudinal axis is parallel with and laterally offset from the chassis central longitudinal axis.

6. The apparatus of claim 5 wherein the another apparatus including the corresponding flat portion comprises another of the surgical instrument apparatus, and wherein the respective flat portions facilitate location of the respective elongate manipulators in proximity for insertion through a common access port positioned to provide access to the body cavity of the patient.

7. The apparatus of claim 5 wherein the actuator chassis includes a transition portion between the manipulator and the actuator chassis, the transition portion configured to laterally displace the control links for coupling to the respective actuators.

8. The apparatus of claim 5 wherein the manipulator comprises at least one end effector control link configured to couple to an end effector, and wherein the actuator chassis comprises at least one end effector actuator coupled to the end effector control link to actuate movements of the end effector.

9. The apparatus of claim 8 wherein the at least one end effector actuator is mounted within the actuator chassis to permit at least one of:
longitudinal movement configured to actuate opening or closing of an end effector; or
rotational movement configured to cause a corresponding rotation of the end effector.

10. The apparatus of claim 9 wherein the at least one end effector actuator comprises a single end effector actuator configured to perform both the longitudinal movement and the rotational movement.

11. The apparatus of claim 8 wherein the at least one end effector control link is routed along a central bore of the actuator chassis.

12. The apparatus of claim 5 wherein the manipulator further comprises:
a rigid portion; and
a first articulated portion configured to cause the movement of the distal end of the manipulator in response to the longitudinal movement of the control links, the first actuatable articulated portion disposed at a distal end of the rigid portion.

13. The apparatus of claim 12 further comprising a second actuatable articulated portion disposed between a proximal end of the rigid portion and the chassis, the second actuatable articulated portion configured to permit the manipulator to be bent to reduce an overall length of the manipulator and actuator chassis during cleaning and sanitizing of the apparatus.

14. A surgical instrument apparatus for performing a surgical procedure within a body cavity of a patient, the apparatus comprising:
an elongate manipulator comprising a distal end configured to receive an end effector and including a plurality of control links extending through the manipulator and configured to cause movement of the distal end of the manipulator in response to movement of the control links in a longitudinal direction generally aligned with a length of the manipulator, wherein the elongate manipulator defines a manipulator central longitudinal axis; and
an actuator chassis disposed at a proximal end of the manipulator, the actuator chassis including a plurality of actuators slidingly mounted with respect to the actuator chassis and configured to move linearly in a direction aligned with the longitudinal direction, each actuator being coupled to one of the control links, the actuators being disposed about a periphery of the actuator chassis and including an outwardly oriented portion configured to couple a drive force to the actuator to cause movement of the control link, wherein the actuator chassis defines a chassis central longitudinal axis, wherein the outwardly oriented portions of the plurality of actuators are each shaped to engage a corresponding drive coupling configured to couple the drive force to the actuator, and wherein an actuator coupling portion of the actuator comprises an actuator protrusion that extends outwardly beyond the periphery of the actuator chassis, and
a drive chassis including a respective plurality of drive couplers configured to couple drive forces to the plurality of actuators, the drive couplers arranged about the periphery of the actuator chassis, each drive coupler comprising:
an open channel portion configured to receive the respective actuator protrusions when the actuator chassis is inserted into the drive chassis; and
a retaining portion configured to receive and retain the respective actuator protrusions when the drive chassis and the actuator chassis are rotated thorough an angle to cause the retaining portions to engage the respective actuator protrusions,
wherein the manipulator central longitudinal axis is parallel with and laterally offset from the chassis central longitudinal axis.

15. The apparatus of claim 14 wherein the drive chassis is configured to permit the manipulator to be inserted through the drive chassis to cause the open channel portions to receive the respective actuator protrusions.

* * * * *